(12) United States Patent
Baru et al.

(10) Patent No.: US 10,537,742 B2
(45) Date of Patent: Jan. 21, 2020

(54) SYSTEM AND METHODS FOR CAPTURE VERIFICATION IN IMPLANTABLE LEADLESS PACEMAKERS

(71) Applicant: BIOTRONIK SE & CO. KG, Berlin (DE)

(72) Inventors: Marcelo Baru, Tualatin, OR (US); Ramprasad Vijayagopal, Sugar Land, TX (US); Alan Fryer, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 201 days.

(21) Appl. No.: 15/851,999

(22) Filed: Dec. 22, 2017

(65) Prior Publication Data

US 2018/0185653 A1 Jul. 5, 2018

Related U.S. Application Data

(60) Provisional application No. 62/441,983, filed on Jan. 4, 2017.

(51) Int. Cl.
*A61N 1/37* (2006.01)
*A61N 1/375* (2006.01)

(52) U.S. Cl.
CPC .......... *A61N 1/371* (2013.01); *A61N 1/3702* (2013.01); *A61N 1/3714* (2013.01);
(Continued)

(58) Field of Classification Search
CPC ........ A61N 1/025; A61N 1/14; A61N 1/3628; A61N 1/365; A61N 1/36521; A61N 1/37;
(Continued)

(56) References Cited

U.S. PATENT DOCUMENTS

| 4,343,312 A | 8/1982 | Cals et al. |
| 4,543,956 A | 10/1985 | Herscovici |

(Continued)

FOREIGN PATENT DOCUMENTS

| WO | 9739794 A1 | 10/1997 |
| WO | 0143819 A1 | 6/2001 |
| WO | 2005089866 A1 | 9/2005 |

*Primary Examiner* — Eugene T Wu
(74) *Attorney, Agent, or Firm* — Laurence A. Greenberg; Werner H. Stemer; Ralph E. Locher

(57) ABSTRACT

A pacing system, which is particularly suitable for implantable leadless pacemakers, applies passively-balanced voltage-based pacing pulses, and periodically performs capture verification (evoked response detection) by following a pacing pulse with a current-based active balancing pulse, and then measuring any evoked response provoked by the pacing pulse. The active balancing pulse reduces residual charge on the electrodes used for pulsing, and thereby reduces polarization artifacts that could obscure measurement of the evoked response at the electrodes. The amplitude and pulse width of the active balancing current pulse are defined by measurements made in a few preceding pulses. The pacemaker preferably detects indicia of cardiac contractility, and performs capture verification only when contractility indicates that the patient is physically inactive and emotionally stable.

13 Claims, 3 Drawing Sheets

(52) U.S. Cl.
CPC ......... *A61N 1/3716* (2013.01); *A61N 1/3756* (2013.01); *A61N 1/37512* (2017.08)

(58) Field of Classification Search
CPC .... A61N 1/3702; A61N 1/3704; A61N 1/371; A61N 1/3712; A61N 1/3714; A61N 1/3716; A61N 1/37205; A61N 1/37241; A61N 1/3756; A61B 5/7217
See application file for complete search history.

(56) References Cited

U.S. PATENT DOCUMENTS

| | | |
|---|---|---|
| 6,865,421 B2 | 3/2005 | Bradley |
| 7,089,049 B2 | 8/2006 | Kerver et al. |
| 7,474,922 B2 | 1/2009 | Hudson |
| 8,214,036 B2 | 7/2012 | Casset |
| 8,340,762 B2 | 12/2012 | Vonk et al. |
| 8,489,188 B2 | 7/2013 | Giorgis et al. |
| 8,801,624 B2 | 8/2014 | Patangay et al. |
| 8,862,231 B2 | 10/2014 | Kirchner et al. |
| 8,923,963 B2 | 12/2014 | Bonner et al. |
| 9,358,387 B2 | 6/2016 | Suwito et al. |
| 2006/0224199 A1* | 10/2006 | Zeijlemaker ........... A61N 1/371 607/11 |
| 2009/0149905 A1 | 6/2009 | Lyden et al. |

* cited by examiner

SYSTEM AND METHODS FOR CAPTURE VERIFICATION IN IMPLANTABLE LEADLESS PACEMAKERS

CROSS-REFERENCE TO RELATED APPLICATION

This application claims the priority, under 35 U.S.C. § 119(e), of provisional patent application No. 62/441,983 filed Jan. 4, 2017; the prior application is herewith incorporated by reference in its entirety.

FIELD OF THE INVENTION

This document concerns an invention relating generally to myocardial evoked response detection, and more specifically to evoked response detection systems suitable for use in implantable leadless pacemakers.

BACKGROUND OF THE INVENTION

Pacemakers are devices implanted in the body to stimulate the heart and regulate its contractions. Many pacemakers have housings which are implanted in the patient's chest or abdomen, and which have leads extending to the heart, wherein electrodes on the leads apply electrical stimulation. The pacemaker typically applies electrical stimulation having a fixed amplitude, one which is chosen with a safety margin that ensures successful "capture," that is, the myocardium exhibits the desired behavior (depolarization) after receiving stimulation (a pacing pulse).

Leadless pacemakers, wherein electrodes are provided directly on the housing, and the housing is sized to be implanted entirely within a chamber of the heart (see U.S. Pat. No. 9,358,387), are growing increasingly popular. A typical design has a pacing electrode at one end, and the housing (the "can"), or a portion thereof, is connected to battery ground so that it can serve the role of the return electrode. Because leadless pacemakers must be made very small for optimal operation—typically smaller than a AAA battery—they are subject to severe engineering constraints regarding the size (and thus capacity) of their components. Because their batteries must be small, the batteries typically have more limited energy storage capacity. One way for a leadless pacemaker to conserve energy, and thus prolong its battery life, is to avoid use of the aforementioned "excess stimulation," and instead utilize an automatic capture control algorithm which finds the minimum stimulation needed to attain successful capture. This is difficult owing to constraints regarding the size and computing ability of its electronics module. In conventional (lead-bearing) pacemakers, automatic capture assessment is typically done by measuring evoked response (ER), which is the electrical signal generated by the depolarization of myocardial cells following a pacing pulse. It is known to be challenging to reliably measure an atrial ER in response to an atrial pacing pulse, as an atrial ER starts approximately 10 ms after pulse delivery, and it has much smaller amplitude than a ventricular ER (which starts around 60 ms following a ventricular pacing pulse). Because the atrial ER signal is small and arises quickly after the atrial pulse is delivered, it can be obscured by polarization artifacts from the atrial pacing pulse: the injection of the atrial pacing pulse leaves residual charge in the interface between the pacing electrode and the myocardial tissue.

Several techniques have been proposed for distinguishing ER signals from polarization artifacts. One approach is to use low-polarization coatings on the pacemaker electrodes, such as fractal iridium (Ir), that provide high Helmholtz double-layer capacities which assist in reducing polarization (and thus artifacts). However, the use of these coatings alone may not be sufficient to reduce artifacts to such an extent that the ER is easily discernable.

Another approach is to simply use different electrodes for pacing and for ER sensing, thereby isolating the polarization at the pacing electrode from the ER sensing electrode. This approach can be difficult to practically implement in a leadless pacemaker, where size/space is critical, thereby making it highly desirable to use the same electrodes for pacing and sensing. Thus, "passive" and "active" charge balancing methods have been developed to discharge the residual charge at the electrode/tissue interface, and better allow use of the same electrode for both pacing and sensing. In contrast to active charge balancing systems, wherein the residual charge is monitored and then battery current is used to negate it, passive charge balancing systems seek discharge without the need for battery current. U.S. Pat. No. 6,044,296 shows passive charge balancing method wherein an extra capacitor is switched in series with the output direct current (DC) blocking capacitor to more quickly discharge the polarization charge after a stimulus pulse. U.S. Pat. No. 8,224,446 uses a passive charge balancing method wherein after potentials resulting from the pacing pulse are attenuated by reducing coupling capacitance. U.S. Pat. No. 8,948,866 teaches a similar technique of minimizing the post-pacing artifact by using a smaller coupling capacitor borrowed from a backup pacing capacitor, or another coupling capacitor from a different pacing channel. This approach also has drawbacks, as the capacitors needed to discharge the residual charge occupy additional space, posing challenges for minimizing the size of the pacemaker.

Yet another approach uses alternative pacing waveforms which reduce polarization effects. U.S. Pat. No. 8,340,762 discusses use of a tri-phasic pulse generation technique to reduce the polarization effects, an approach originally proposed by U.S. Pat. Nos. 4,343,312 4,543,956 teaches utilizing a biphasic current pulse with automatic and dynamic compensation utilizing integrators. A disadvantage of these approaches is that they use current-based methods for stimulation pulses and for subsequent balancing (i.e., negation of polarization), and for better power efficiency and battery life, leadless pacemakers are preferably voltage-based stimulation devices, like traditional pacemakers.

Several references also teach analog and digital filtering methods for isolating ER signals from artifacts, e.g., U.S. Pat. Nos. 7,474,922 and 7,089,049. Many others disclose different signal post-processing techniques to eliminate the artifact, or discuss use of the polarity of the post-pacing response signal to confirm whether capture occurred or not (e.g. U.S. Pat. No. 6,865,421). These approaches also have drawbacks, as second order band-pass filters in the input circuit of a pacemaker may distort a polarization artifact to such an extent that it is falsely interpreted as an evoked response (ER). Special digital filtering techniques are also not preferred for implementation in a leadless pacemaker given the limited computing resources typically available.

Other approaches detect capture via detection of (mechanical) heart motion, rather than via detection of (electrical) ER. U.S. Pat. No. 5,549,652 describes sensing capture by detecting motion of the cardiac wall using a sensor present in a lead. Published international patent application WO 2005/089866 A1 proposes detection of capture in a cardiac cavity by detecting contraction from a signal representing endocardial acceleration (EA) delivered by an accelerometer sensor situated in a lead. U.S. Pat. No. 8,214,036 presents improvements to the detection described in international patent application WO 2005/089866 A1, with focus on atrial capture. U.S. Pat. Nos. 8,489,188 and 8,862,231 teach similar approaches based on EA signals. U.S. Pat. No. 8,801,624 describes use of an implantable heart sound sensor (e.g. an accelerometer) configured to initiate a paced cardiac contraction. Similarly, U.S. Pat. No. 8,923,963 describes a leadless atrial pacemaker having a mechanical sensor that generates signals indicative of contraction of a ventricle.

While some of the obstacles to achieving effective capture verification while at the same time furthering pacemaker miniaturization will undoubtably decrease as further developments are made in electronics miniaturization and in battery technology, it would nonetheless be useful to have additional approaches which at least reduce some of the drawbacks noted above. In particular, it would be useful to have effective capture verification methods available for use in leadless pacemakers designed for implantation in the atrium, where the electrical signals indicating capture are much more challenging to measure than in the ventricle.

SUMMARY OF THE INVENTION

The invention, which is defined by the claims set out at the end of this document, is addressed to pacing methods, as well as a pacemaker (or subassemblies thereof), which seek to address the foregoing problems. It should be understood that where the invention is described as a "pacemaker," this term is intended to encompass any devices which provide a heart stimulation function. Thus, the invention encompasses devices whose primary functions may be other than pacing, so long as such devices at least occasionally provide heart stimulation. Also, while the invention is particularly intended for implementation in implantable leadless pacemakers, it can be implemented in other types of pacemakers as well.

Preferred versions of the invention involve methods and systems for detecting whether or not a pacing pulse results in myocardium capture, as evidenced by an evoked response (ER). These methods and systems seek to provide a voltage-based pacing scheme with a charge balancing phase that can be switched from passive balancing during normal pacing to an active current-based balancing technique during capture verification. The active charge balancing phase seeks to bring the post-pace open-circuit potential (OCP) difference between the pacing and return electrodes to its pre-pace value, thereby minimizing the polarization artifact caused by the biphasic pacing & balancing stimulus and allowing for robust ER sensing. The amplitude of the charge balancing pulse is such that it does not affect the threshold of the voltage pacing pulse compared to the threshold achieved with the normal passive balancing phase; the width of the charge balancing pulse is no longer than 5 ms or so (at most), so that early ER (e.g., atrial ER) might be more easily detected; and it utilizes pulses delivered during at least one, and preferably several, preceding cardiac refractory periods to determine a current pulse amplitude and pulse width to be used for charge balancing. These preceding pulses can be anodic and cathodic pulses delivered at the pacing electrode, with alternating passive and active charge balancing phases.

A pacemaker can then occasionally apply these methods to detect ER and verify capture, preferably on a periodic basis (e.g., once per hour). Since a patient's physical activity and emotional stress can reduce pacing thresholds, preferred versions of the invention also seek to perform ER sensing when the patient is at rest/ease, with the patient's rest/ease state preferably being indicated by the patient's cardiac contractility. For example, ER might be measured over a period during each hour when cardiac contractility indicates the patient's heart is in a resting state. Contractility might be measured using an electromechanical sensor (e.g., an accelerometer) hermetically contained within the pacemaker housing, with its output being filtered to distinguish endocardial acceleration from body movement. Alternatively (or additionally), contractility might be measured using an electrochemical sensor, such as an amplifier or other circuitry for analyzing the open-circuit potential (OCP) difference between the pacing electrodes during diastole/expansion. Scheduled ER sensing might then only proceed if the contractility signal illustrates that the patient is not in a physically active and/or emotionally distressed state.

Preferred versions of the invention also seek to provide methods for ER signal processing and capture verification that do not require complicated mathematical operations or sophisticated computing power, thereby reducing processor burdens.

In one aspect, a heart pacing method is provided including:

a. performing passively balanced voltage-based pacing, wherein during each pace:
   (1) a pacing pulse having a predefined pacing voltage is delivered to the heart from a pacing electrode; and
   (2) any residual charge between the pacing electrode and the heart is allowed to passively dissipate before a subsequent pacing pulse is delivered to the heart;

b. performing capture verification, the capture verification including the following steps in sequence:
   (1) delivering a response-evoking pulse having the predefined pacing voltage to the heart from the pacing electrode;
   (2) performing a current-based active balancing step wherein an active balancing pulse is delivered to the heart from the pacing electrode, the active balancing pulse having:
       (a) a predefined current, and
       (b) a predefined pulse width, wherein the current and the pulse width are defined by measurements made following pulses occurring prior to the response-evoking pulse;
   (3) measuring any evoked response provoked by the response-evoking pulse.

In another aspect, a device for pacing a heart is provided. The device is configured to:

a. perform passively balanced voltage-based pacing, wherein during each pace:
   (1) a pacing pulse having a predefined pacing voltage is delivered to the heart from a pacing electrode; and
   (2) any residual charge between the pacing electrode and the heart is allowed to passively dissipate before a subsequent pacing pulse is delivered to the heart;

b. perform capture verification, the capture verification including the following steps in sequence:
   (1) delivering a response-evoking pulse having the predefined pacing voltage to the heart from the pacing electrode;
   (2) performing a current-based active balancing step wherein an active balancing pulse is delivered to the heart from the pacing electrode, the active balancing pulse having:
       (a) a predefined current, and (b) a predefined pulse width, wherein the current and the pulse width are defined by measurements made following pulses occurring prior to the response-evoking pulse;

(3) measuring any evoked response provoked by the response-evoking pulse.

According to a preferred embodiment of the heart pacing method according to the present invention, the capture verification further includes the following steps prior to delivering the response-evoking pulse:

a. a post-balancing voltage determination step including:
   (1) delivering a testing pulse having the predefined current to the heart from the pacing electrode, and
   (2) measuring a balancing voltage between the pacing electrode and a return electrode;
b. a balancing pulse width determination step including:
   (1) delivering a pacing pulse having the predefined pacing voltage to the heart from the pacing electrode;
   (2) delivering a trial balancing pulse having the predefined current from the pacing electrode to the heart until the voltage between the pacing electrode and the return electrode reaches the post-balancing voltage; and
   (3) determining the pulse width of the trial balancing pulse.

Preferably, the predefined current of the heart pacing method according to the invention is less than the ratio of:
a. the pacing voltage, and
b. a path resistance between the pacing electrode and the return electrode.

According to embodiments of the heart pacing method according to the invention, the predefined current is less than 25% of the ratio.

Preferably, the heart pacing method according to the invention further includes the preceding step of measuring the path resistance between the pacing electrode and the return electrode.

According to an aspect of the present invention, the heart pacing method further includes the subsequent steps of:
a. measuring the path resistance between the pacing electrode and the return electrode;
b. redefining the predefined current in dependence on the measured path resistance; and
c. repeating the step of performing capture verification.

In one embodiment of the heart pacing method according to the present invention, capture verification is performed several times daily.

Preferably, capture verification of the heart pacing method according to the invention is performed when the patient is at rest.

According to embodiments of the present invention, the heart pacing method further includes the steps of:
a. obtaining an indication of the patient's heart contractility, and
b. thereafter performing the capture verification step when the patient's heart contractility is below a predefined contractility threshold.

Preferably, the heart pacing method of the present invention is performed by a leadless pacemaker.

According to an aspect of the present invention, a heart pacing method is provided including:
a. performing passively balanced voltage-based pacing, wherein during each pace:
   (1) an electrical pacing pulse having a predefined pacing voltage is delivered to the heart between a pacing electrode and a return electrode; and
   (2) any residual charge between the pacing electrode and the heart is allowed to passively dissipate before a subsequent pacing pulse is delivered to the heart;
b. performing capture verification, the capture verification including the following steps in sequence:
   (1) a balancing voltage determination including:
      (a) delivering an electrical testing pulse having a predefined current from the pacing electrode to the heart, the predefined current being less than the ratio of the pacing voltage to a path resistance between the pacing electrode and the return electrode;
      (b) measuring a balancing voltage between the pacing electrode and the return electrode;
   (2) a balancing pulse width determination step including:
      (a) delivering an electrical pacing pulse having the predefined pacing voltage to the heart between the pacing electrode and the return electrode;
      (b) delivering an electrical trial balancing pulse having the predefined current from the pacing electrode to the heart until the voltage between the pacing electrode and the return electrode reaches the balancing voltage; and
      (c) determining the pulse width of the trial balancing pulse;
   (3) a capture verification step including:
      (a) delivering an electrical response-evoking pulse having the predefined pacing voltage to the heart between the pacing electrode and the return electrode;
      (b) delivering an electrical active balancing pulse from the pacing electrode to the heart, the active balancing pulse having:
         i. the predefined current, and
         ii. the pulse width of the trial balancing pulse;
      (c) measuring any evoked response provoked by the response-evoking pulse.

In yet another aspect, a device for pacing a heart is disclosed. The device is configured to:
a. perform passively balanced voltage-based pacing, wherein during each pace:
   (1) an electrical pacing pulse having a predefined pacing voltage is delivered to the heart between a pacing electrode and a return electrode; and
   (2) any residual charge between the pacing electrode and the heart is allowed to passively dissipate before a subsequent pacing pulse is delivered to the heart;
b. perform capture verification, the capture verification including the following steps in sequence:
   (1) a balancing voltage determination including:
      (a) delivering an electrical testing pulse having a predefined current from the pacing electrode to the heart, the predefined current being less than the ratio of the pacing voltage to a path resistance between the pacing electrode and the return electrode;
      (b) measuring a balancing voltage between the pacing electrode and the return electrode;
   (2) a balancing pulse width determination step including:
      (a) delivering an electrical pacing pulse having the predefined pacing voltage to the heart between the pacing electrode and the return electrode;
      (b) delivering an electrical trial balancing pulse having the predefined current from the pacing electrode to the heart until the voltage between the pacing electrode and the return electrode reaches the balancing voltage; and
      (c) determining the pulse width of the trial balancing pulse;

(3) a capture verification step including:
   (a) delivering an electrical response-evoking pulse having the predefined pacing voltage to the heart between the pacing electrode and the return electrode;
   (b) delivering an electrical active balancing pulse from the pacing electrode to the heart, the active balancing pulse having:
      i. the predefined current, and
      ii. the pulse width of the trial balancing pulse;
   (c) measuring any evoked response provoked by the response-evoking pulse.

Further advantages, features, and objects of the invention will be apparent from the following detailed description of the invention in conjunction with the associated drawings.

DETAILED DESCRIPTION OF PREFERRED VERSIONS OF THE INVENTION

Figure 1:
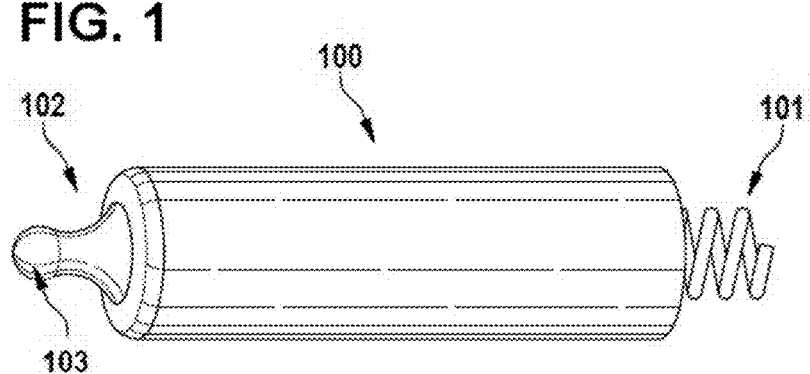
FIG. 1 is a diagrammatic, perspective view of an implantable leadless pacemaker suitable for use with the invention.

The invention is preferably implemented in a leadless pacemaker, with an exemplary leadless pacemaker 100 being illustrated in FIG. 1. The pacemaker 100 includes a pacing electrode 101 at one end, with the electrode 101 being configured to be anchored in the myocardium, and a return electrode 102 at its opposite end. The return electrode 102 may include a hitch 103, which facilitates implantation and explanation of the leadless pacemaker 100, as part of its active area. To decrease polarization, both electrodes 101 and 102 are preferably coated with fractal iridium (Ir). Electrically, the Helmholtz capacitance presented by electrode 101 (when implanted) is much smaller than the one presented by electrode 102 to reduce the pacing threshold and avoid anodic stimulation at the return electrode 102. The remainder of the case/can of the leadless pacemaker 100, apart from electrode 102, is electrically isolated (e.g. parylene coated), such that the electrodes 101 and 102 perform similarly to electrodes along a traditional bipolar pacemaker pacing lead.

Figure 2:
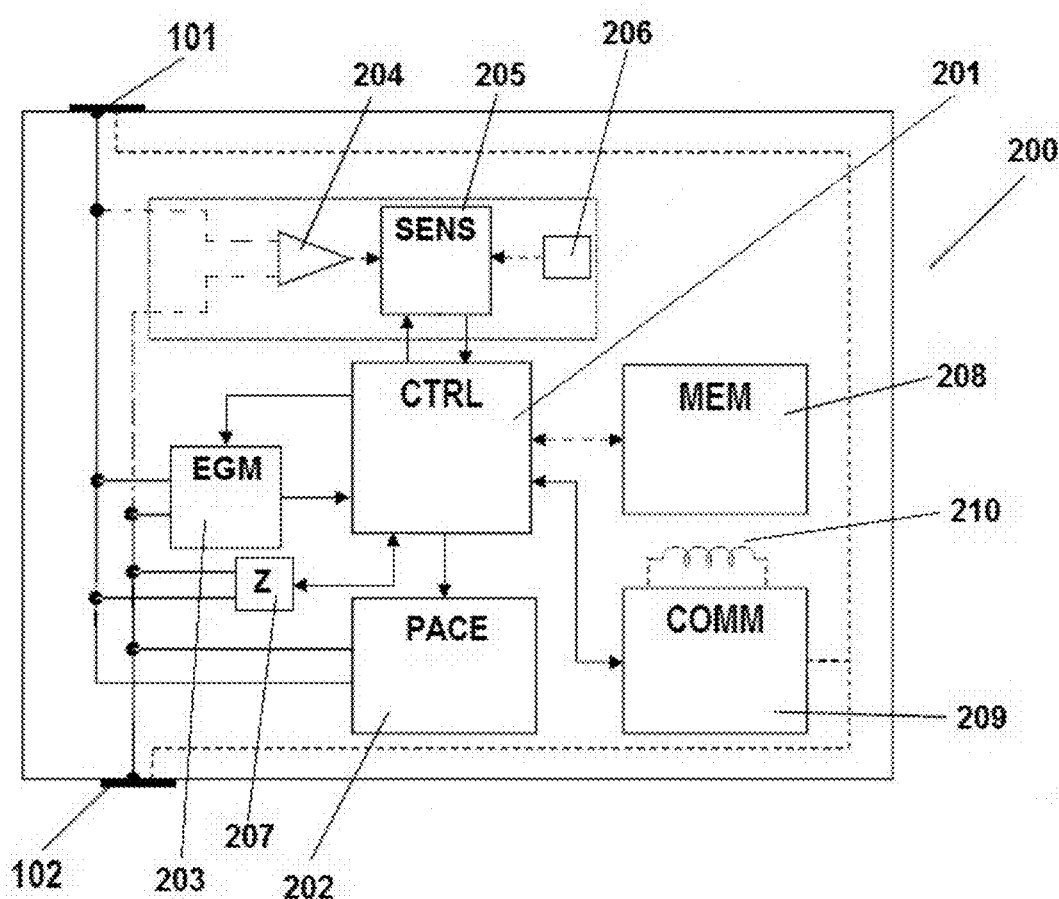
FIG. 2 is a block diagram of exemplary preferred components of electronics within a leadless pacemaker such as that of FIG. 1.

FIG. 2 provides a schematic diagram of exemplary preferred components of the electronics 200 within the leadless pacemaker 100. A control unit 201 manages pacing unit 202 and electrogram (EGM) unit 203, which are connected to the electrodes 101 and 102. The electrodes 101 and 102 may be further connected to inputs of amplifier 204, which is capable of measuring the open-circuit potential (OCP) difference between the electrodes 101 and 102 for myocardium contractility evaluation, as described in U.S. patent publication No. 2016/0066849 A1. The measured potential is provided to a sensing unit 205 that provides a contractility signal to the control unit 201. Alternatively (or additionally), the electronics 200 could include a different type of contractility sensor 206—for example, an electromechanical contractility sensor such as an accelerometer—for cardiac contractility evaluation.

The control unit 201 also manages an impedance measurement unit 207, which permits measuring the impedance between electrodes 101 and 102, preferably using sub-threshold biphasic current pulses in a known manner. The control unit 201 may be further connected to a memory 208 and to a communication unit 209 allowing transmission of data to and/or from the electronics 200 to a programming unit or other device located outside the patient's body. The communication unit 209 could use, for example, intra-body galvanic communication (e.g., Z-COMM) via the electrodes 101 and 102, coil-based inductive communication via coil 210, or radio frequency or ultrasonic communications.

Figure 3:
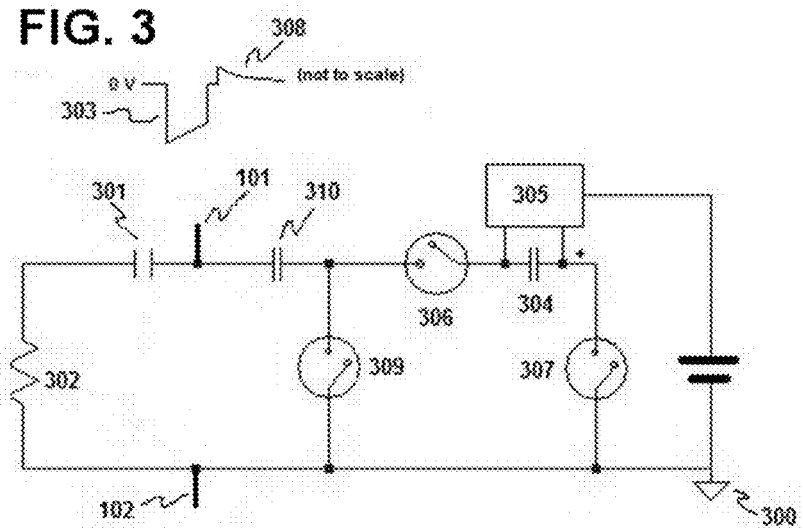
FIG. 3 is a circuit diagram illustrating exemplary conventional front-end (pacing) electronics that might be used in pacemaker electronics, such as the pacing unit 202 of FIG. 2.

FIG. 3 illustrates exemplary conventional front-end (pacing) electronics usable in the pacing unit 202 of the leadless pacemaker 100, along with an electrical model of the in-vivo impedance between the pacing electrode 101 and the return electrode 102. The return electrode 102 is preferably permanently tied to the battery negative terminal 300 (system ground). The interface between the pacing electrode 101 and tissue is represented by capacitor 301. The capacitance of the tissue-electrode interface at the return electrode 102 is much larger, and is not shown. The resistor 302 models intra-electrode impedance, i.e., tissue resistance to pacing. To deliver a pacing pulse 303, the capacitor 304 is precharged (with the illustrated polarity) to the programmed pacing voltage by the voltage step-up/down circuit represented by the unit 305 (e.g., a charge pump). When the control unit 201 indicates it is time to deliver a pace, electrical connections to unit 305 are floated and analog switches 306 and 307 are closed by the control unit 201. This forces the pacing electrode 101 below ground 300, allowing current to flow from return electrode 102 through tissue resistance 302, resulting in the cathodic stimulation pulse 303 at the pacing electrode 101. Following the end of the stimulation pulse 303, autoshort 308 is performed by opening the analog switches 306 and 307 and closing analog switch 309 for tens of ms, thereby passively discharging the tissue-electrode capacitance 301 and the output direct current (DC) blocking capacitor 310.

Because the pacing electrode 101 and return electrode 102 are preferably each configured with a small window/area to achieve large pacing impedances 302 (typically 700 to 1,000 Ω) and thereby minimize power consumption, and considering output pacing capacitances 310 are in the order of 10 µF, a passive charge balancing phase will typically require at least 21 ms (3τ) to balance the charge. This period is long enough to obscure earlier ER, whereby the use of the temporary current-based active balancing phase is discussed below. The output capacitor 310 has many functions, but it is primarily used to avoid DC flow through tissue and to reduce the equivalent capacitance for autoshort 308.

Figure 4:
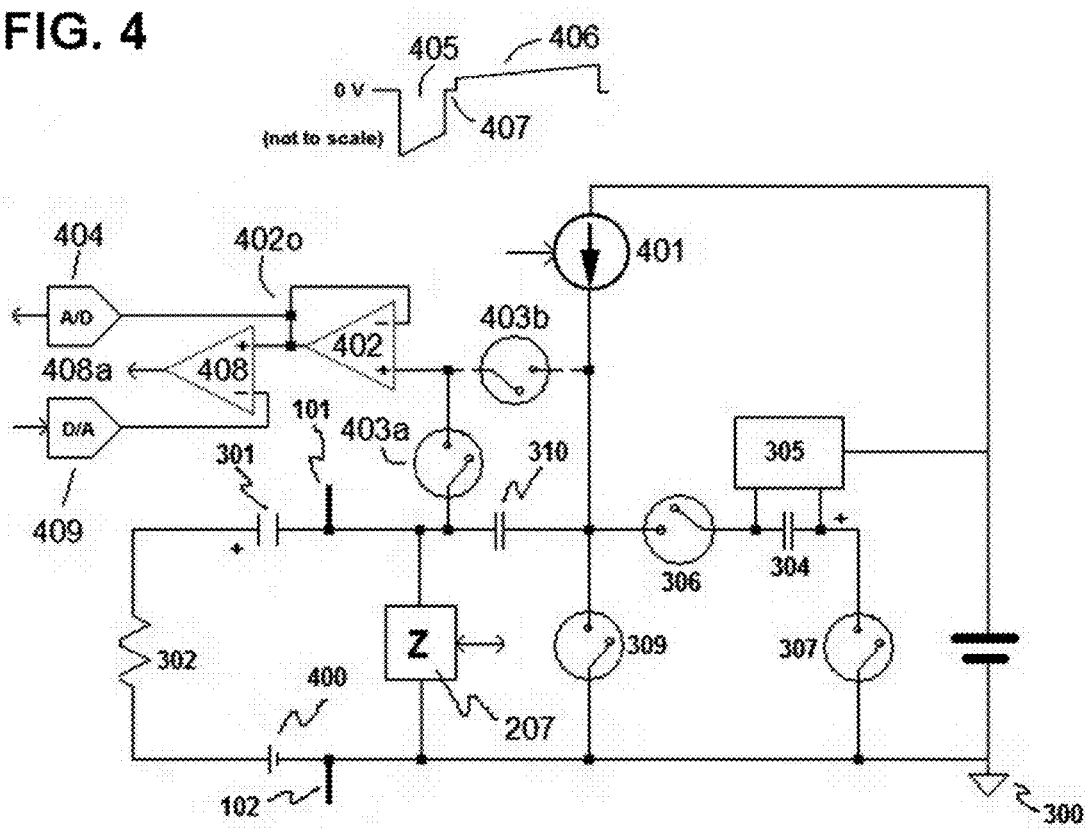
FIG. 4 is a circuit diagram illustrating exemplary preferred front-end (pacing) electronics that might be used in a pacing unit such as the pacing unit 202 of FIG. 2.

FIG. 4 illustrates exemplary front-end (pacing) electronics which are preferred for use in the pacing unit 202 of the pacemaker 100 in lieu of the conventional arrangement of FIG. 3. Again, an electrical model of the in-vivo impedance between the pacing electrode 101 and the return electrode 102 is shown. An added voltage 400, not included in FIG. 3, represents the open-circuit potential (OCP) difference ($\Delta V_{OCP}$) between the pacing electrode 101 and the return electrode 102. This voltage 400 is typically within ±100 mV when the pacing electrode 101 and the return electrode 102 are formed of different materials, but it is smaller when the electrodes 101 and 102 are formed of the same material and only differ in area. The current source 401 permits injection of anodic active balancing pulses into the pacing electrode 101 with respect to the return electrode 102.

Following implantation of the pacemaker 100, passively-balanced voltage-based pacing can occur as discussed above, with cathodic pacing pulses being delivered at the pacing electrode 101, and with passive discharge of residual charge on the tissue-electrode capacitance 301 and the output direct current (DC) blocking capacitor 310.

When capture verification is to be performed—or beforehand, if desired—the control unit 201 measures the impedance between the pacing electrode 101 and the return electrode 102, i.e., across tissue resistance 302, via the impedance measurement unit 207 utilizing biphasic sub-threshold current pulses.

The control unit 201 then calculates an initial value for the active balancing current to later be supplied by the current source 401, this current being denoted $I_{401i}$, as the ratio of the programmed pacing voltage $V_{pace}$ to some multiple of the tissue resistance $R_{302i}$ (the resistance multiplier here being chosen as 8):

$$\text{i) } I_{401i} = \frac{V_{Pace}}{8R_{302i}}. \tag{1}$$

The resistance multiplier is used to reduce the amplitude of the initial active balancing current $I_{401i}$, permitting an active charge balancing phase for capture verification that does not affect the pacing threshold. As will be seen below, the biphasic pulse used to evaluate capture, having a pacing voltage phase and a balancing current phase, behaves similarly to a normal voltage pacing pulse using passive charge balancing in terms of pacing threshold. The calculation of the initial active balancing current $I_{401i}$ is preferably performed by a microcontroller within or associated with the control unit 201. This microcontroller is preferably turned off or placed in an ultra-low-power state during normal operation of the pacemaker 100, and is occasionally powered up to assist with capture verification tasks (including signal processing as described below). The initial current value $I_{401i}$ could instead be calculated in another manner, as by transmitting the measured initial impedance value $R_{302i}$ to an external programmer via the communication unit 209, with the external programmer calculating $I_{401i}$ and programming it into the control unit 201 via the communication unit 209.

A step, referred to herein as a post-balancing voltage determination step, is then performed to determine the balancing potential between the electrodes 101 and 102 when the charge of a voltage pacing pulse has been completely balanced. During the refractory period two cycles prior to a scheduled capture verification, the control unit 201 turns on analog buffer 402, closes analog switch 403a (and possibly an optional second analog switch 403b), and injects the programmed $I_{401i}$ for a short period (e.g. 30.5 µs). At the end of this pulse, the control unit 201 digitizes the output 402o ($V_{402o}$) of the analog buffer 402 via the analog-to-digital converter (A/D) 404. Since the pulse width is short, the charge accumulated by the capacitor 301 is small and may be neglected. As a result:

$$\text{i) } V_{402o} \approx \Delta V_{OCP} + R_{302i} I_{401i} \tag{2}$$

which is defined as $V_{StopBal}$, i.e. the voltage reached at the electrode 101 when the charge of a pacing pulse has been completely balanced.

Following the termination of the step above, all circuitry utilized is powered down and/or disconnected, and the analog switch 309 is closed with a longer autoshort period (308 in FIG. 3), e.g., for a period of 5τ.

During the heart's next refractory period, the pulse width of the yet-to-be-delivered active balancing pulse is determined. A therapy pacing pulse 405 having amplitude $V_{Pace}$ is delivered, followed by an active charge balancing phase 406 with current $I_{401i}$. The inter-phase delay 407 may be equal to or greater than the one between the end of pulse 303 and the start of autoshort 308. A timer is started at the beginning of the active charge balancing phase 406, and analog switch 403a is closed to compare, via an analog comparator 408, the pulse electrode 101 voltage (at output 402o) with saved voltage $V_{StopBal}$, generated by the digital-to-analog converter (D/A) 409. Since the accumulated voltage on the tissue-electrode capacitance 301 due to the pacing pulse 405 has the sign shown in FIG. 4, the comparator output 408a will change from ground voltage 300 to a high logical level. When that occurs, the control unit 201 stops the active charge balancing phase 406 and records the timer value defining the active charge balancing pulse width ($PW_{IBal}$).

During the next cycle, in which capture verification will occur, the control unit 201 delivers a therapy pacing pulse 405, actively balances with a current-based pulse with parameters $I_{401i}$ and $PW_{IBal}$, and immediately measures the evoked response (ER) via the EGM unit 203.

Preferably, capture verification is periodically performed, e.g., once every hour. Since the tissue impedance 302 (and open-circuit potential 400) may change over time, current 401 ($I_{401i}$) may require adjustment so that its contribution to the active charge balancing phase amplitude does not exceed $V_{Pace}/8$ (or some other fraction of $V_{Pace}$ which is unlikely to affect the capture threshold).

During a refractory period close in time to a scheduled capture verification, the control unit 201 re-measures the impedance and saves the new value $R_{302n}$. If a microcontroller is present in the control unit 201, a new $I_{401n}$ may be calculated as per equation (2) above, and the steps for initial capture verification above are repeated to obtain a new ER. Alternatively, the new $I_{401n}$ may be determined in a computationally efficient manner using a lookup table. To illustrate, the difference between the initial and most recent resistance values $R_{302}$ is defined by:

$$\text{i) } \Delta R = R_{302i} - R_{302n} \tag{3}$$

For positive $\Delta R$, the control unit 201 may generate a table with values of $R_{302n}$ divided by multiples of the aforementioned resistance multiplier. Assuming the resistance multiplier is 8 (as in the example above), the table might include $R_{302n}/64$, $R_{302n}/32$, $R_{302n}/16$, etc., as well as possibly including intermediate values generated by addition of these values. $\Delta R$ is then compared with the entries in this table. Assuming $\Delta R$ is between positions $R_{302n(x)}$ and $R_{302n(x+1)}$ where $R_{302n(x)} < R_{302n(x+1)}$, $I_{401n}$ is selected from a parallel table entries generated using $I_{401i}/64$, $I_{401i}/32$, $I_{401i}/16$, etc. as:

$$\text{i) } I_{401n} = I_{401i} + I_{401i(x)} \tag{4}$$

This guarantees that $$\text{i)} \quad I_{401n} \leq \frac{V_{Pace}}{8R_{302n}}. \quad (5)$$

A similar process can be used when $\Delta R$ is negative, in which case $I_{401n} = I_{401i} - I_{401i(x+1)}$.

The pacemaker 100 could instead only start performing capture verification once impedance has stabilized following implantation, in which case it may be sufficient to simply utilize $I_{401i}$.

Analog switches 403a and 403b do not require low impedance, unlike switches 306, 307, and 309. However, because the switches 403a/403b are on the opposite side of the output DC blocking capacitor 310, they require low charge injection and a driving technique that maintains DC leakage below the present safety standards (100 nA under single-fault conditions). The analog buffer 402 presents high impedance and low offset, and single-fault protected inputs to avoid placing a DC voltage at electrode 101 when switch 403a is closed. The comparator 408 also presents low offset, and preferably sub-$\mu$s detection with an overdrive of a few mV.

Figure 5:
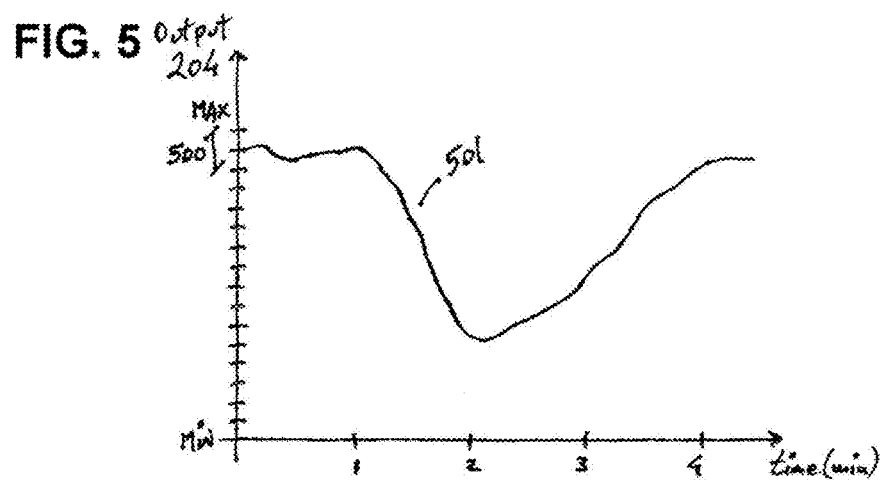
FIG. 5 is a graph depicting an open-circuit potential (OCP) between the pacing and return electrodes 101 and 102, as measured by the amplifier 204 in FIG. 2, which can provide an indication of myocardium contractility.

Scheduled (or otherwise automated) capture verification preferably only proceeds if the patient is at rest/ease, for example, where the sensing unit 205 provides an indication of at rest/ease myocardium contractility to the control unit 201. If the amplifier 204 is used to measure the open-circuit potential (OCP) for myocardium contractility evaluation, as described in U.S. patent publication No. 2016/0066849 A1, capture verification may proceed if the output of amplifier 204 (during diastole) is within a voltage window 500 (FIG. 5) for a period (e.g., a minute) prior to a scheduled verification. Physical activity or emotional stress will cause a sudden change (such as at 501) in the output of amplifier 204, which will inhibit capture verification. If this arises, the control unit 201 may delay the scheduled capture verification, and continue monitoring the sensing unit 205 to perform the delayed capture verification when the sensing unit 205 indicates that the output of amplifier 204 is within window 500 (i.e., that the patient is at rest/ease).

If an accelerometer or other electromechanical sensor 206 is instead used instead for cardiac contractility evaluation, capture verification may proceed if the output of the sensor 206 is below a predetermined contractility threshold for a period prior to a scheduled verification. For example, if the peak-to-peak endocardial acceleration (EA) is below a predefined level, the scheduled ER sensing for capture verification can proceed.

Figure 6:
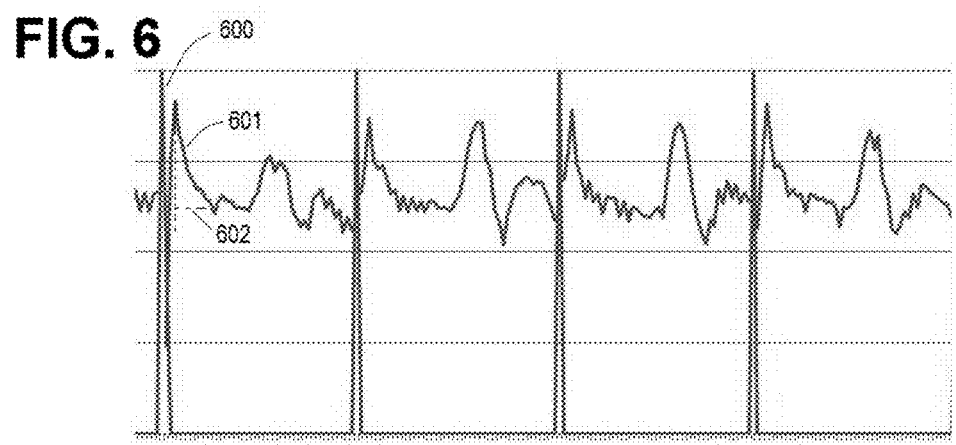
FIG. 6 is a graph illustrating exemplary capture paces 600 and resulting ventricular ERs 601.
Figure 7:
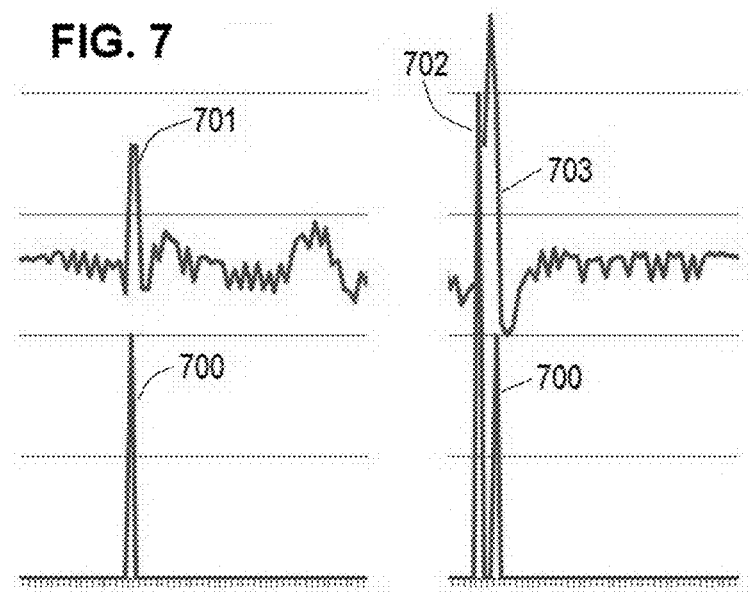
FIG. 7 is a graph showing a recorded appearance of an intrinsic sensed event 700 alone (at 701), and within a fused event 703 wherein an intrinsic sensed event 700 is overlapped by a capture pace 702.

Preferably, the control unit 201 overrides the detected natural cardiac cycle by 10 pulses per minute to avoid fusion beats from overlapping with capture verification paces. FIG. 6 illustrates ventricular ERs 601 recorded between electrodes 101 and 102 following capture paces 600. FIG. 7 compares the recorded appearance of an intrinsic sensed event 700 alone (at 701), and also within a fused event 703, i.e., capture pace 702 overlaps intrinsic sensed event 700.

The events 601 can be identified by implementing a morphological filter in the EGM unit 203 to detect ER signals 601. A particularly preferred filter is a black Top-Hat transform, which can detect ER signals 601 within 100 ms of a capture pace 600, and with no false positives. This transform cleans the ER signal 601, adjusts it to its baseline, and dilation and erosion operations can provide the difference in value and in number of samples between the maximum of the ER signal 601 and its valley, thereby permitting the detection of certain widths 602 characteristic of an evoked response (ER) 601 to a capture pace 600. This type of filtering has the advantage that its operations are based on maxima and minima of the signal 601. Such operations are useful for implementation in leadless pacemakers 100 because they have low computational cost.

The description set out above is merely of exemplary preferred versions of the invention, and it is contemplated that numerous additions and modifications can be made. These examples should not be construed as describing the only possible versions of the invention, and the true scope of the invention will be defined by the claims included in any later-filed utility patent application claiming priority from this provisional patent application.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

100 Leadless pacemaker
101 Pacing electrode
102 Return electrode
103 Hitch
200 Electronics within leadless pacemaker
201 Control unit
202 Pacing unit
203 Electrogram unit
204 Amplifier
205 Sensing unit
206 Contractility sensor
207 Impedance measurement unit
208 Memory
209 Communication unit
210 Coil
300 Ground
301 Tissue-electrode capacitance
302 Tissue resistance
303 Stimulation pulse
304 Capacitor
305 Voltage processing unit
306, 307, 309 Analog switches
308 Autoshort
400 Added voltage
401 Current source
402 Analog buffer
403a, 403b Analog switches
404 A/D converter
405 Therapy pacing pulse
406 Charge balancing phase
407 Interphase delay
408 Analog comparator
408a Comparator output
409 D/A converter
500 Voltage window
501 Sudden signal change
600 Capture pace
601 Evoked response
602 Signal width characteristic of evoked response
700 Recorded intrinsic sensed event 701 Intrinsic sensed event
702 Capture pace
703 Fused event

The invention claimed is:

1. A heart pacing method, which comprises the steps of:
 a. performing passively balanced voltage-based pacing, wherein during each pace performing the further steps of:
  (1) delivering a pacing pulse having a predefined pacing voltage to a heart from a pacing electrode; and
  (2) allowing any residual charge between the pacing electrode and the heart to passively dissipate before a subsequent pacing pulse is delivered to the heart;
 b. performing a capture verification, the capture verification including the following steps in sequence:
  (1) delivering a response-evoking pulse having the predefined pacing voltage to the heart from the pacing electrode;
  (2) performing a current-based active balancing step wherein an active balancing pulse is delivered to the heart from the pacing electrode, the current-based active balancing pulse having:
   (a) a predefined current; and
   (b) a predefined pulse width, wherein the predefined pulse current and the predefined pulse pulse width are defined by measurements made following pulses occurring prior to the response-evoking pulse; and
  (3) measuring any evoked response provoked by the response-evoking pulse.

2. The heart pacing method of claim 1, wherein the capture verification further includes the following steps prior to delivering the response-evoking pulse:
 a. performing a post-balancing voltage determination step which further includes:
  (1) delivering a testing pulse having the predefined current to the heart from the pacing electrode; and
  (2) measuring a balancing voltage between the pacing electrode and a return electrode;
 b. performing a balancing pulse width determination step which includes:
  (1) delivering the pacing pulse having the predefined pacing voltage to the heart from the pacing electrode;
  (2) delivering a trial balancing pulse having the predefined current from the pacing electrode to the heart until a voltage between the pacing electrode and the return electrode reaches the post-balancing voltage; and
  (3) determining a pulse width of the trial balancing pulse.

3. The heart pacing method according to claim 1, wherein the predefined current is less than a ratio of:
 the pacing voltage; and
 a path resistance between the pacing electrode and a return electrode.

4. The heart pacing method according to claim 3, wherein the predefined current is less than 25% of the ratio.

5. The heart pacing method according to claim 3, which further comprises measuring the path resistance between the pacing electrode and the return electrode.

6. The heart pacing method according to claim 3, which further comprises the subsequent steps of:
 measuring the path resistance between the pacing electrode and the return electrode;
 redefining the predefined current in dependence on the measured path resistance; and
 repeating a performance of the capture verification step.

7. The heart pacing method according to claim 1, which further comprises performing the capture verification step several times daily.

8. The heart pacing method according to claim 1, which further comprises performing the capture verification step when a patient is at rest.

9. The heart pacing method according to claim 1, which further comprises the steps of:
 obtaining an indication of a patient's heart contractility; and
 thereafter performing the capture verification step when the patient's heart contractility is below a predefined contractility threshold.

10. The heart pacing method according to claim 1, which further comprises providing a leadless pacemaker for performing the method.

11. A heart pacing method, which comprises the steps of:
 a. performing passively balanced voltage-based pacing, wherein during each pace:
  (1) delivering an electrical pacing pulse having a predefined pacing voltage to a heart between a pacing electrode and a return electrode; and
  (2) allowing any residual charge between the pacing electrode and the heart to passively dissipate before a subsequent pacing pulse is delivered to the heart;
 b. performing capture verification, the capture verification including the following steps in sequence:
  (1) performing a balancing voltage determination further including:
   (a) delivering an electrical testing pulse having a predefined current from the pacing electrode to the heart, the predefined current being less than a ratio of the pacing voltage to a path resistance between the pacing electrode and the return electrode;
   (b) measuring a balancing voltage between the pacing electrode and the return electrode;
  (2) performing a balancing pulse width determination step further including:
   (a) delivering an electrical pacing pulse having the predefined pacing voltage to the heart between the pacing electrode and the return electrode;
   (b) delivering an electrical trial balancing pulse having the predefined current from the pacing electrode to the heart until a voltage between the pacing electrode and the return electrode reaches the balancing voltage; and
   (c) determining the pulse width of the electrical trial balancing pulse;
  (3) performing a capture verification step further including:
   (a) delivering an electrical response-evoking pulse having the predefined pacing voltage to the heart between the pacing electrode and the return electrode;
   (b) delivering an electrical active balancing pulse from the pacing electrode to the heart, the electrical active balancing pulse having:
    i. the predefined current, and
    ii. the pulse width of the electrical trial balancing pulse; and
   (c) measuring any evoked response provoked by the electrical response-evoking pulse.

12. A device for pacing a heart, the device being configured to:
 a. perform passively balanced voltage-based pacing, wherein during each pace:

(1) a pacing pulse having a predefined pacing voltage is delivered to the heart from a pacing electrode; and (2) any residual charge between the pacing electrode and the heart is allowed to passively dissipate before a subsequent pacing pulse is delivered to the heart;

b. perform capture verification, the capture verification including the following steps in sequence:

(1) delivering a response-evoking pulse having the predefined pacing voltage to the heart from the pacing electrode;

(2) performing a current-based active balancing step wherein an active balancing pulse is delivered to the heart from the pacing electrode, the active balancing pulse having:
(a) a predefined current; and
(b) a predefined pulse width, wherein the predefined current and the predefined pulse width are defined by measurements made following pulses occurring prior to the response-evoking pulse; and (3) measuring any evoked response provoked by the response-evoking pulse.

13. A device for pacing a heart, the device being configured to:

a. perform passively balanced voltage-based pacing, wherein during each pace:

(1) an electrical pacing pulse having a predefined pacing voltage is delivered to the heart between a pacing electrode and a return electrode; and (2) any residual charge between the pacing electrode and the heart is allowed to passively dissipate before a subsequent pacing pulse is delivered to the heart;

b. perform capture verification, the capture verification including the following steps in sequence:

(1) a balancing voltage determination including:
(a) delivering an electrical testing pulse having a predefined current from the pacing electrode to the heart, the predefined current being less than a ratio of the pacing voltage to a path resistance between the pacing electrode and the return electrode;
(b) measuring a balancing voltage between the pacing electrode and the return electrode;

(2) a balancing pulse width determination step including:
(a) delivering an electrical pacing pulse having the predefined pacing voltage to the heart between the pacing electrode and the return electrode;
(b) delivering an electrical trial balancing pulse having the predefined current from the pacing electrode to the heart until a voltage between the pacing electrode and the return electrode reaches the balancing voltage; and
(c) determining a pulse width of the trial balancing pulse;

(3) a capture verification step including:
(a) delivering an electrical response-evoking pulse having the predefined pacing voltage to the heart between the pacing electrode and the return electrode;
(b) delivering an electrical active balancing pulse from the pacing electrode to the heart, the active balancing pulse having:
 i. the predefined current; and
 ii. the pulse width of the trial balancing pulse;
(c) measuring any evoked response provoked by the electrical response-evoking pulse.

\* \* \* \* \*